United States Patent
Lee

(10) Patent No.: US 12,115,081 B1
(45) Date of Patent: Oct. 15, 2024

(54) SPINAL INTERBODY IMPLANT WITH CONTROLLED EXPANSION

(71) Applicant: James Lee, Los Altos, CA (US)

(72) Inventor: James Lee, Castro Valley, CA (US)

( * ) Notice: Subject to any disclaimer, the term of this patent is extended or adjusted under 35 U.S.C. 154(b) by 0 days.

(21) Appl. No.: 16/807,097

(22) Filed: Mar. 2, 2020

Related U.S. Application Data

(60) Provisional application No. 62/812,969, filed on Mar. 2, 2019.

(51) Int. Cl.
*A61F 2/44* (2006.01)
*A61F 2/30* (2006.01)

(52) U.S. Cl.
CPC .. *A61F 2/4425* (2013.01); *A61F 2002/30131* (2013.01); *A61F 2002/30579* (2013.01); *A61F 2002/3093* (2013.01); *A61F 2002/443* (2013.01)

(58) Field of Classification Search
CPC ........ A61F 2/44; A61F 2/4425; A61F 2/4455; A61F 2002/30579; A61F 2002/30131; A61F 2002/443
See application file for complete search history.

(56) References Cited

U.S. PATENT DOCUMENTS

| | | | |
|---|---|---|---|
| 9,737,411 B2 | 8/2017 | Loebl et al. | |
| 9,820,865 B2 | 11/2017 | Sharabani et al. | |
| 2013/0190876 A1 | 7/2013 | Drochner et al. | |
| 2017/0156885 A1 | 6/2017 | Zur et al. | |
| 2017/0202679 A1 | 7/2017 | Butler et al. | |
| 2018/0344476 A1* | 12/2018 | Koch | A61F 2/44 |

FOREIGN PATENT DOCUMENTS

WO  WO-2008044057 A1 *  4/2008 ........... A61F 2/4465

* cited by examiner

*Primary Examiner* — Christopher D. Prone

(57) ABSTRACT

An expandable spinal interbody implant having a base member and a displaceable member connected by a screw driven linkage mechanism. The implant may include mechanisms for controlling the implant throughout its full range of expansion and retraction to prevent formation of the implant into undesired profiles in the intervertebral space. The displaceable element may be overlapped with the base in a fully expanded state. Alternatively, the displaceable element may exist fully outside of the base. The displaceable element may be hinged and bent in conjunction with the linkage based implant expansion.

19 Claims, 12 Drawing Sheets

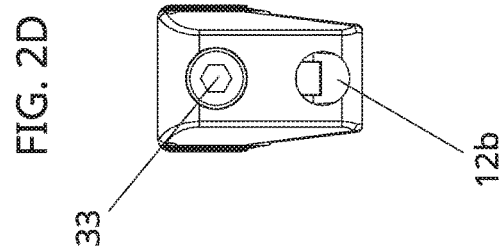
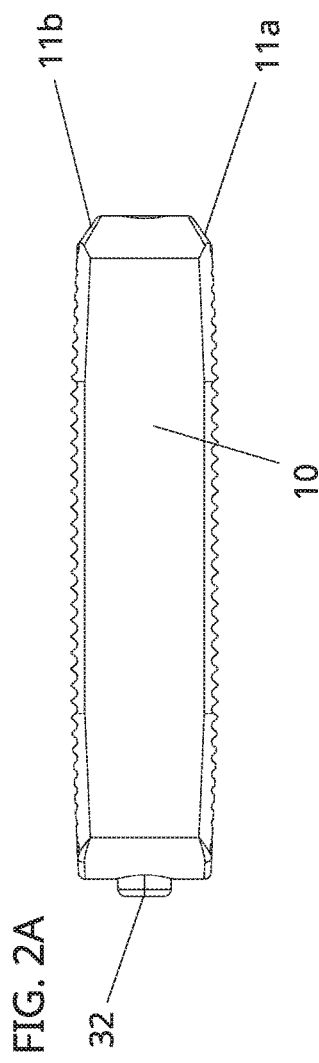
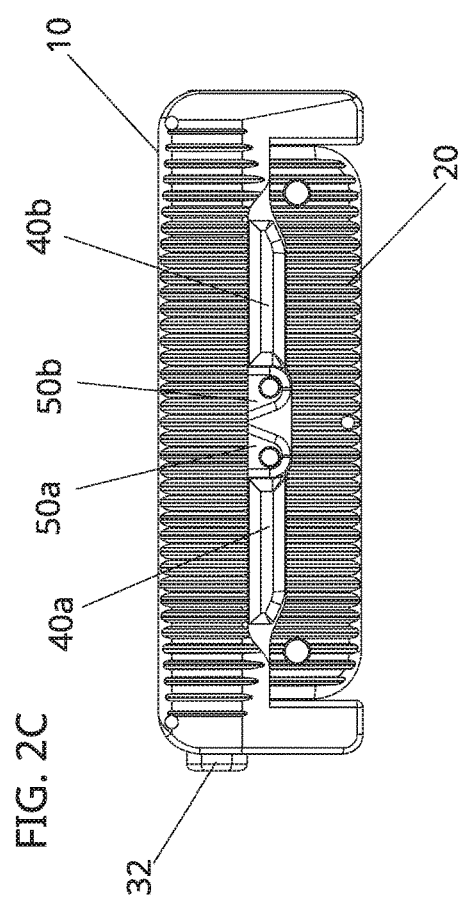
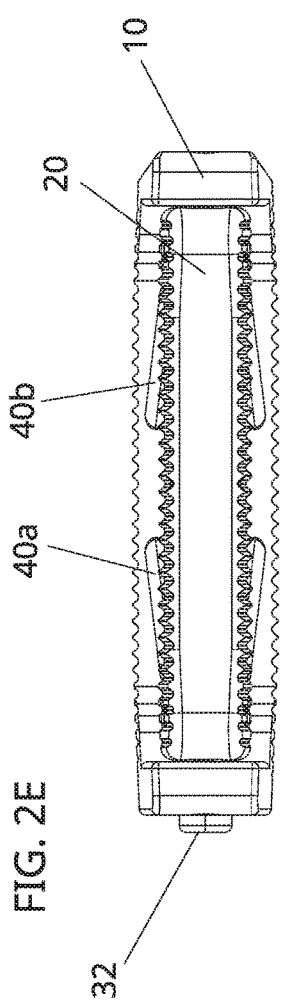
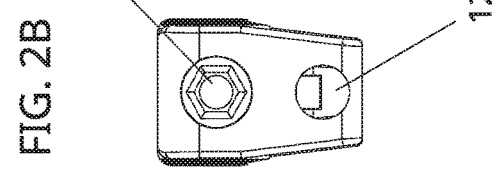

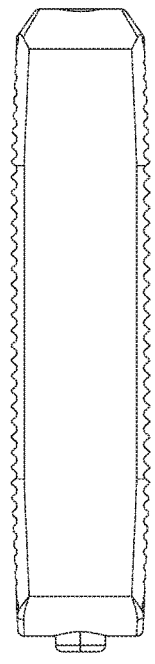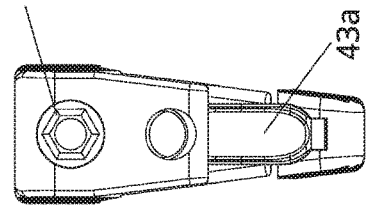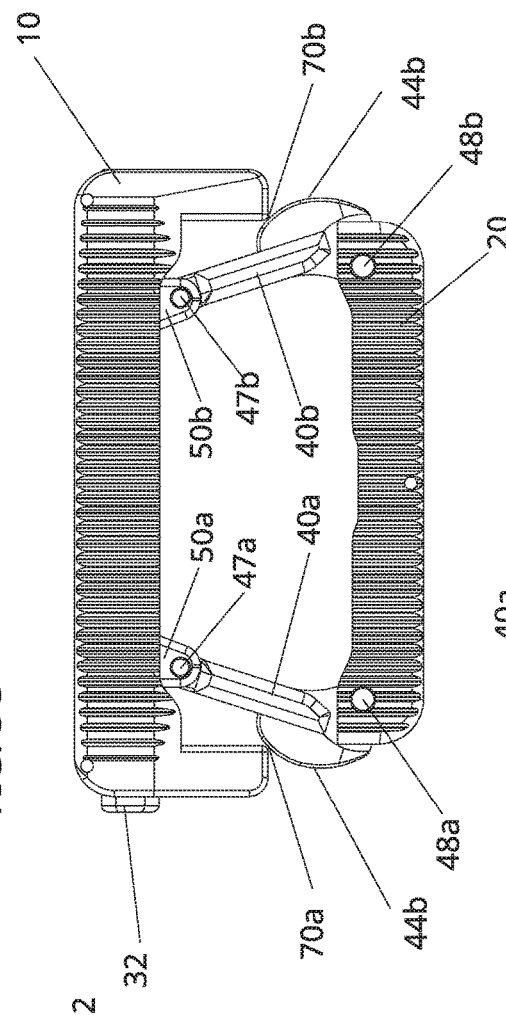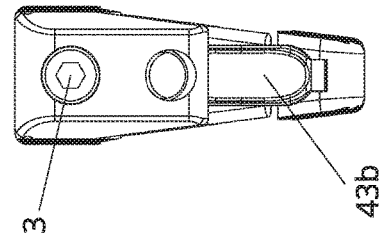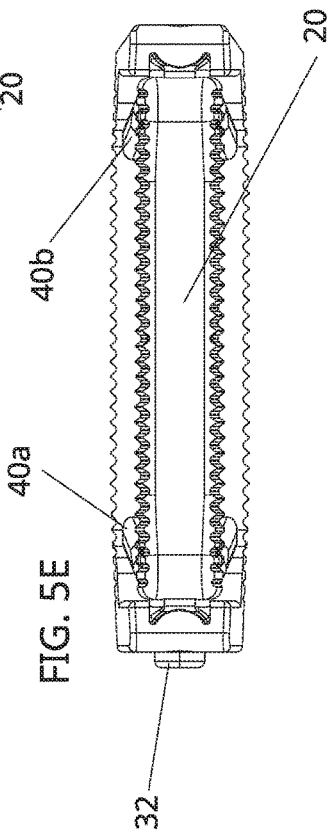

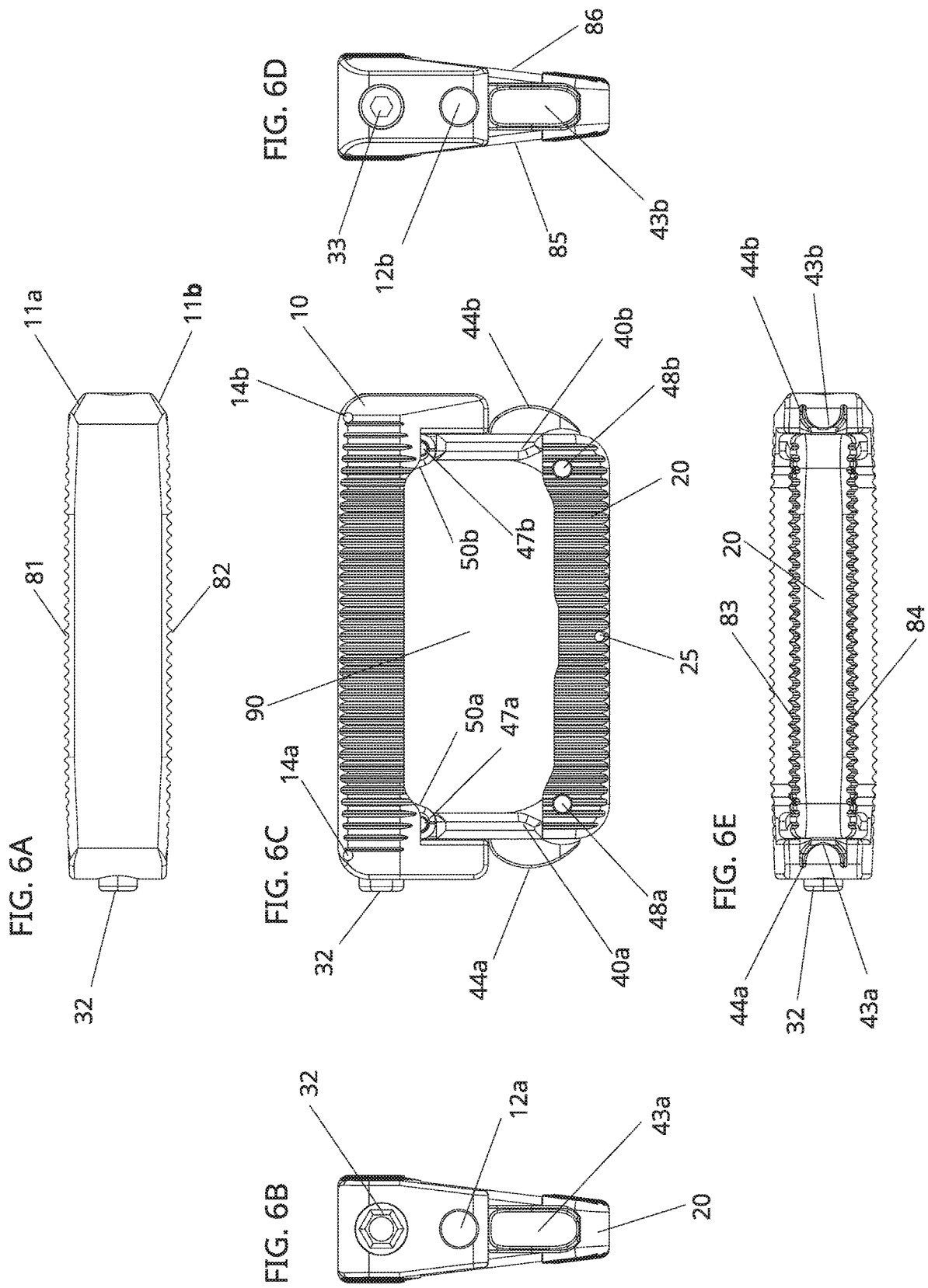

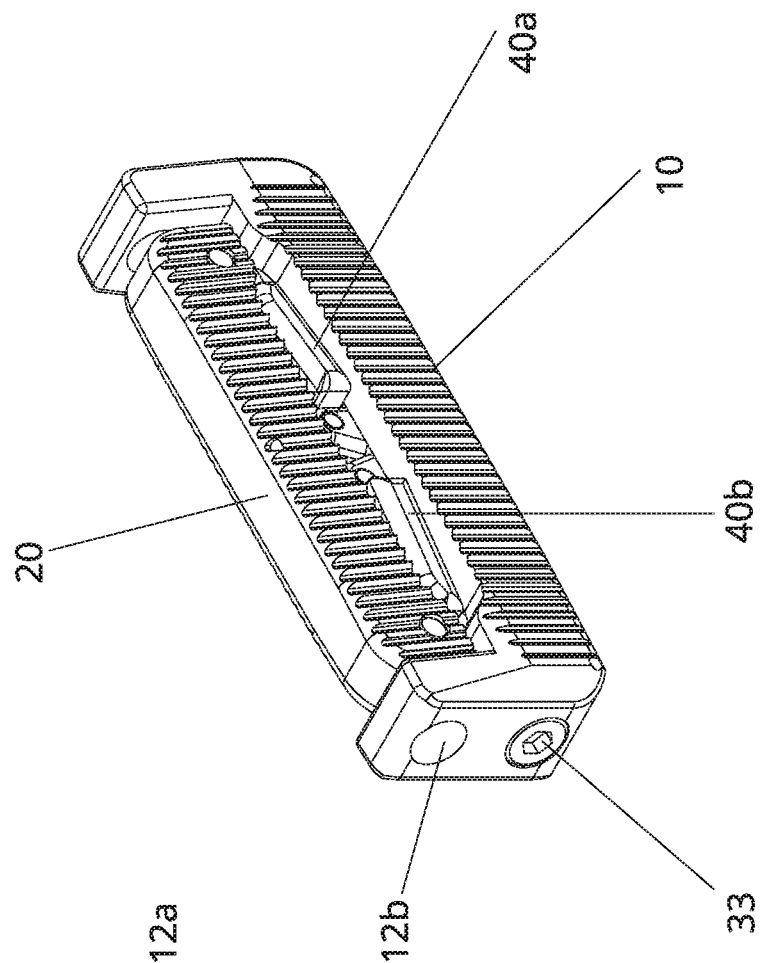
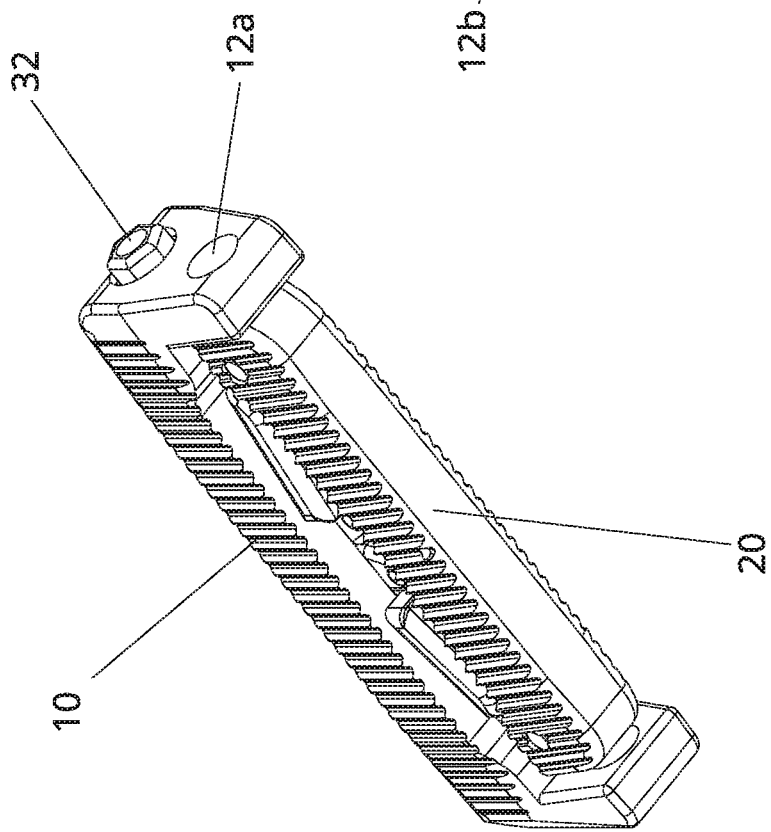

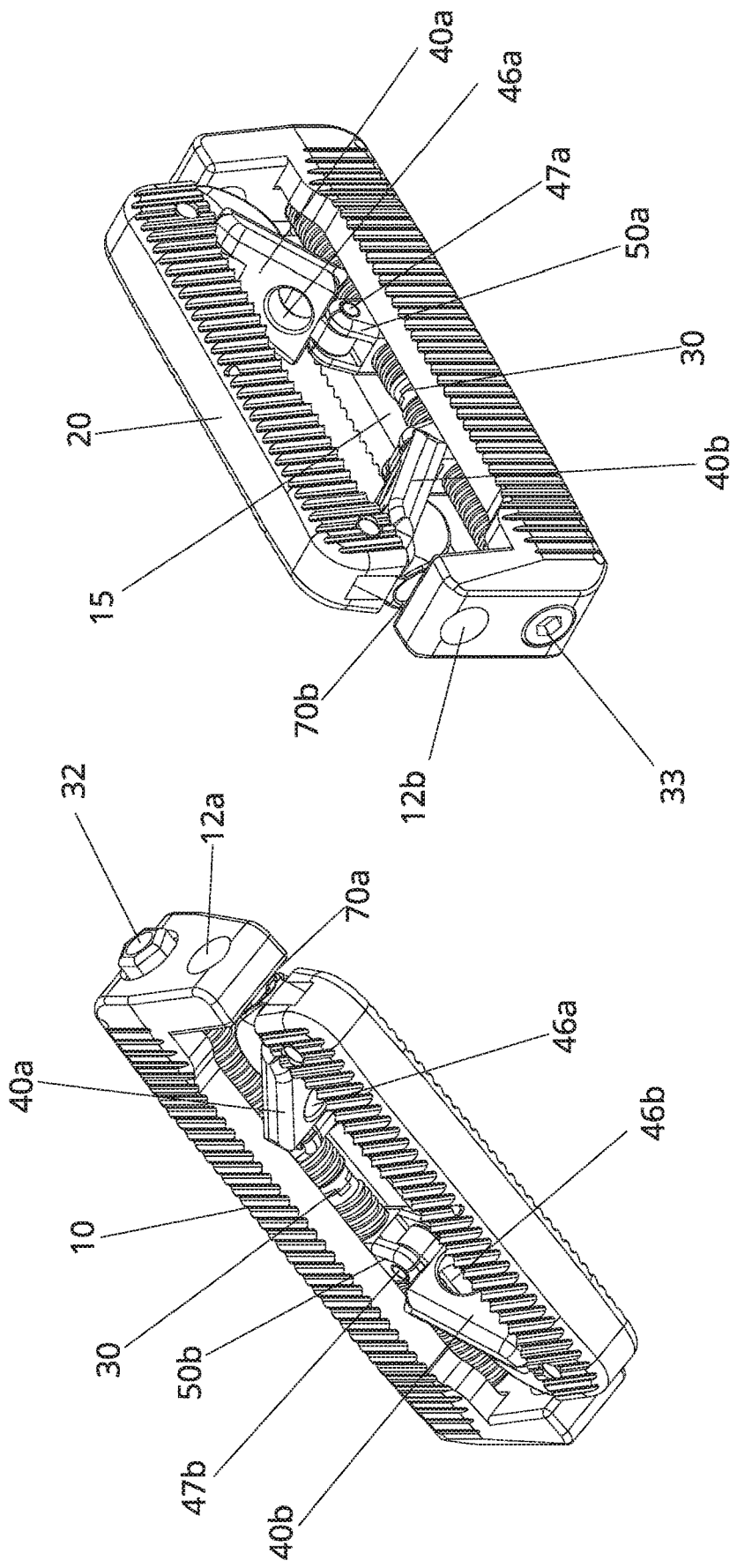

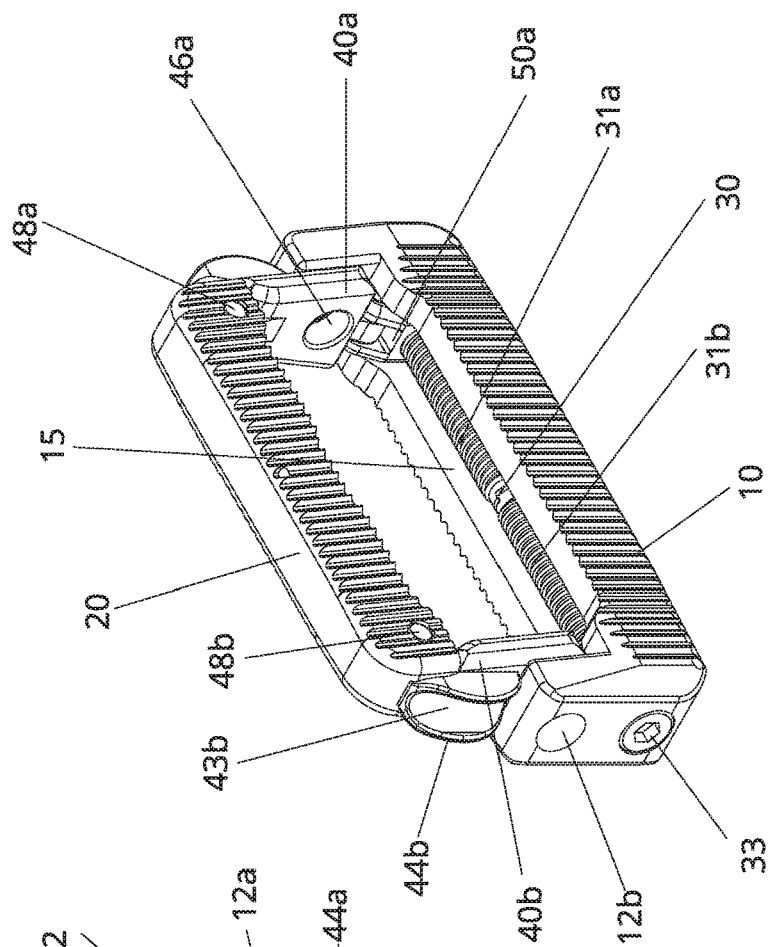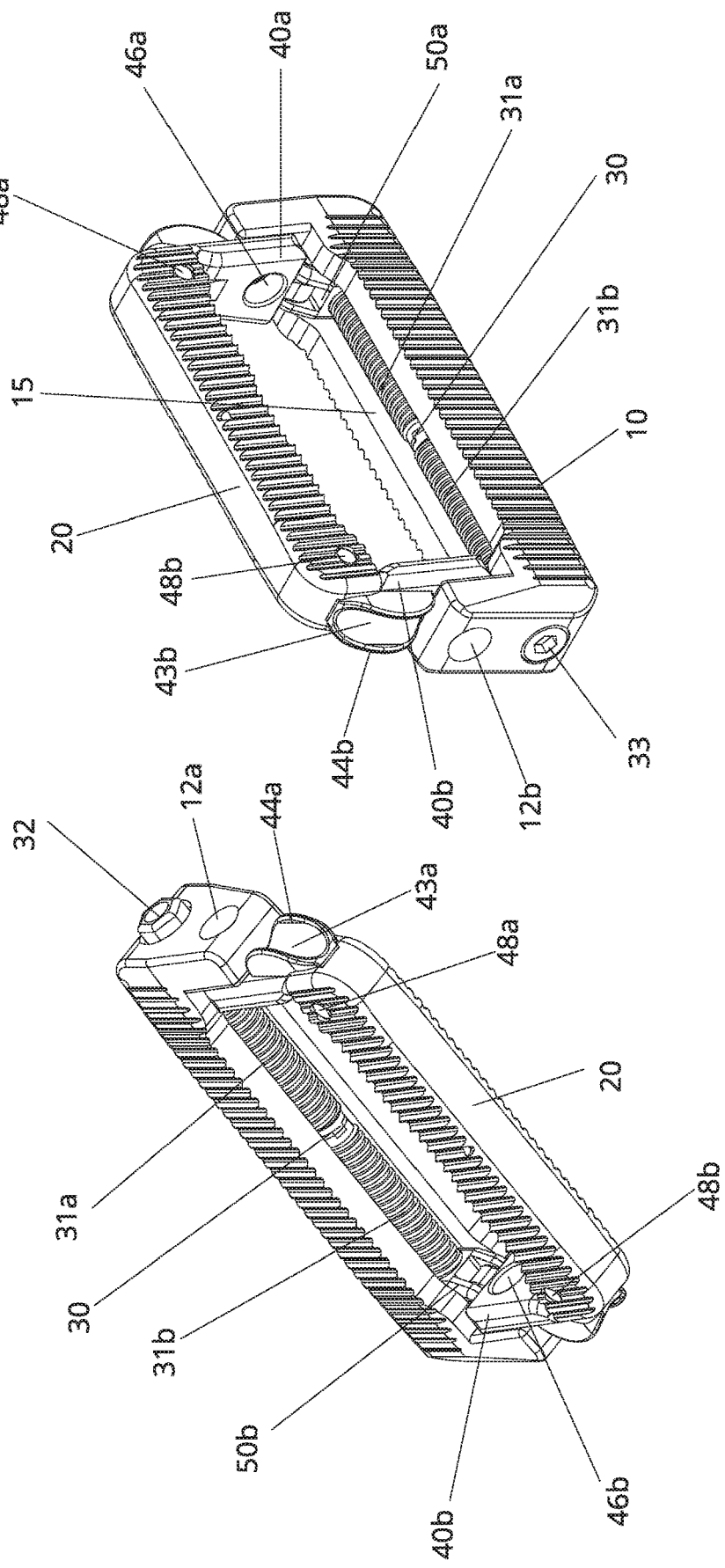

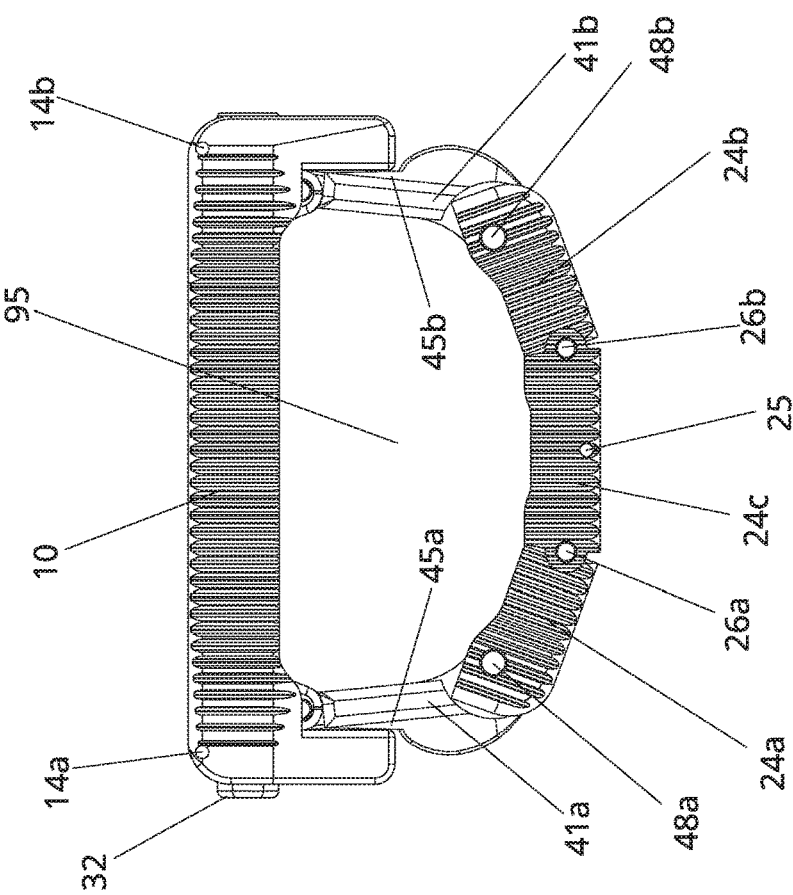
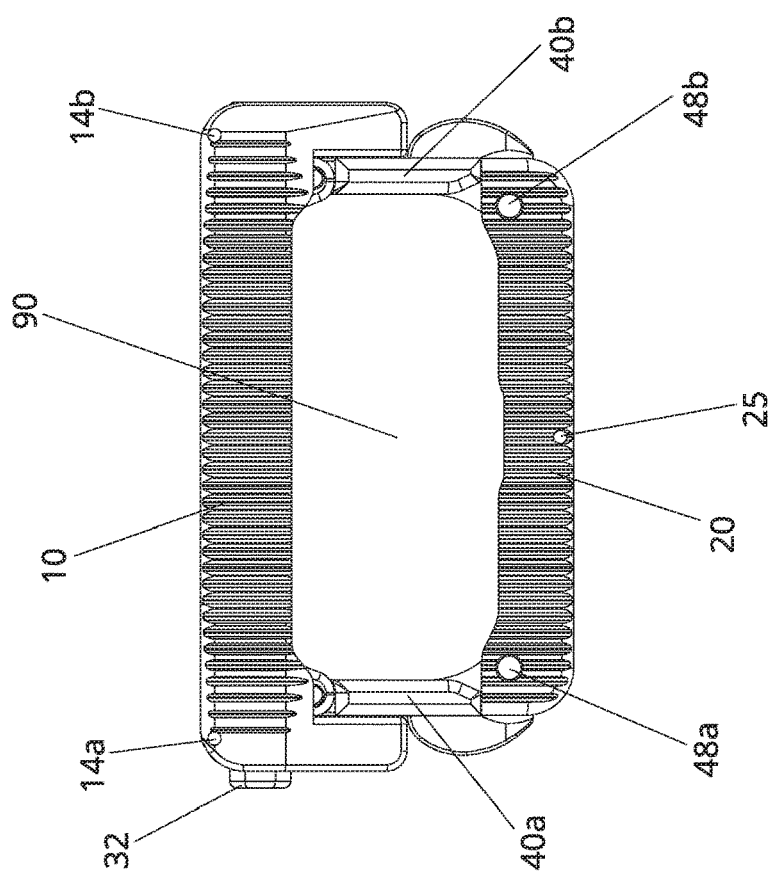

SPINAL INTERBODY IMPLANT WITH CONTROLLED EXPANSION

PRIORITY CLAIM

This application claims priority, to the fullest extent permitted by law, of provisional patent application 62/813,969, in the name of the same inventor, titled "Spinal body implant with controlled expansion", hereby incorporated by reference as if fully set forth herein.

COPYRIGHT NOTICE

A portion of the disclosure of this patent document contains material subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

This background is provided as a convenience to the reader and does not admit to any prior art or restrict the scope of the disclosure or the invention. This background is intended as an introduction to the general nature of technology to which the disclosure or the invention can be applied.

Field of the disclosure. This Application generally relates to spinal interbody implants, such as spinal implants that provide techniques for adjusting their expansion within the implanted space in the body when treating a spinal condition.

In a vertebrate spine, the spinal disc and/or vertebral bodies may be displaced or damaged due to age, trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. A spinal interbody implant, which may also be referred to as an interbody spacer or intervertebral implant, can be inserted into the cavity created where the intervertebral disc was removed to help maintain height of the spine and/or restore stability to the spine. An interbody implant may also provide a lordotic correction to the curvature of the spine. An expandable interbody implant provides a less invasive option to treat these conditions.

Related art. An example of an interbody implant that has been used historically is a fixed dimension spacer, which is typically is packed with morselized bone or bone-growth-inducing biological filler materials before insertion into the prepared disc. In order to adequately support the adjacent vertebrae and provide stability to the spine, it is beneficial for the implant to be as large in footprint as possible. However, a significant disadvantage of a large fixed dimension spacer is that it requires a more invasive surgical procedure for implantation, leading to a higher probability of patient injury and longer recovery time. Conversely, if a smaller fixed dimension spacer is used for a less invasive entry into the disc, the implant may not provide enough footprint area to adequately support the vertebral endplates and may subside into the vertebrae, negating the intended disc height restoration and support between affected vertebral bodies.

In order to provide for a large footprint interbody implant while addressing the surgical invasiveness of fixed cages, expandable implants are designed to be inserted into the disc in a collapsed state and expanded in their footprint in-situ. While several expandable spinal interbody implants already exist in the market, significant tradeoffs and compromises are often made to accommodate the expansion mechanism of these implant designs. One common tradeoff is overt complexity of the design, which can impact manufacturability, cost and reliability. Some implants compromise patient safety if they do not provide a controllable and predictable expansion, or if they cannot retract back to a collapsed state once expanded for an adjustment or revision. Another tradeoff is the need to train the clinician with an overly complicated and specialized installation procedure which may prolong surgical time and result in less than optimal surgical outcomes. Yet another compromise is compensating for a design that is not inherently robust by using materials that are not ideal for the application. In short, there are often many tradeoffs made in the pursuit of designing expanding implants for spinal surgery, and there is still a need for a new implant that provides for the potential benefits of an expanding implant while minimizing common tradeoffs.

Abandoned U.S. Patent Application 20130190876A1 to Drochner discloses a spinal interbody implant design which is able to expand using a link arm mechanism. The disadvantages to this design are that in the first shown embodiment, the link arms converge toward the center of the implant during implant expansion, resulting in an inadequately small enclosure for biological filler material relative to its overall footprint while leaving the elongated base and displacing element substantially unsupported at their corners during expansion. Thus, this implant design would be relatively weak in its ability to expand into the tight confines of a collapsed disc and the small enclosure for biological filler would detract from the probability of successful fusion. If an alternative embodiment were to be imagined (not shown in the application) whereby the link arms separate to the outside edges of the implant instead of the center, then no means are provided to control the expansion path and prevent the displacing element from rocking or folding to one side or the other relative to the base element. In surgery, this could be a critical disadvantage because an implant that expands unpredictably within a collapsed disc could become dislodged from its intended position, negating its intended clinical benefit. A mispositioned expanded implant could also be difficult or even impossible to retract and recover to adjust its positioning, especially through a minimally invasive access opening that is commonly utilized in such surgeries. Even if the implant can be fully expanded to the desired position, no means are provided to rigidly maintain the link arms in the final desired position so as to provide stable support for resisting shear or torsional loads of the spine. In the same application, a third embodiment is shown wherein the link arms are pivotably anchored to the ends of the base, the displacing element is connected to the link arms through pin slots, and the link arms are pushed to swing them to the expanded configuration. This design also suffers from the same problem of the displacing element having an undefined and uncontrolled expansion path, as the pins in the slots are free to move laterally as well as rotationally during implant expansion. In addition, there is no means to retract this implant as the link arms can only be pushed and not pulled.

U.S. Patent Application 20170156885A1 to Zur has many similarities to the third embodiment provided by Drochner. While Zur provides an implant design with an even larger expanded footprint than Drochner, it still suffers from having the same pin-slot arrangement on the displacing element and its accompanying uncontrolled lateral movement problems. An additional shortcoming of Zur is that because of the U shape of the base, the displaceable element would not be able to retract back into a collapsed state if it is shifted laterally out of alignment with the base. An alternate embodiment provided by Zur does show a means of using a protruding pin and arcuate channel arrangement in the displacing element and the pivoting arms respectively to control the expansion path of the displacing member. However, in practice this feature is likely to bind during movement, would be difficult to implement in device assembly, and the intersection of multiple complex mechanical elements occupying the same space that comprise the implant height would necessarily increase overall implant height, limiting the range of implant heights that could treat a full range of clinically relevant disc sizes, especially on the small end. Another shortcoming of Zur is that the only potential path for inserting biological filler into the implant in situ is a tortuous path, which would make expeditious insertion of filler material difficult. In addition, the double sliding pin arrangement necessarily leaves large openings or hollows in the displacing element to accommodate the link arms, which may be disadvantageous for containing biological filler material. In Zur, the enclosure provided for biological filler is also interrupted by the shown link arm actuators, which makes it less optimal for packing biological filler using the provided biological filler insertion hole.

U.S. Pat. No. 9,820,865B2 to Sharabani is also a spinal interbody implant design that expands using a linkage mechanism. In its claims, the linkage mover elements are externally threaded and engaged to internal threads cut into the base. In combination with the claim that the link arm pivot pins are engaged to the linkage mover by annular grooves and the base by sliding slots, this design also suffers from having many mechanical elements stacked together in the same space that comprise the implant height, largely limiting this design from addressing the full range of clinically relevant disc heights, especially on the small end. This design also does not allow controllable expansion of the displacing element beyond its physical overlap with the base, limiting its expansion ratio and thus its utility for providing a large footprint for supporting the vertebral endplates. In addition, biological filler is necessarily designed to be inserted through a coaxial hole in the threaded linkage mover instead of through the base body, which is not only a tortuous path like Zur but also results in an undesirable compromise between how large the biological filler material hole can be compared to how low in height the implant could be. An adequately sized filler hole is an important practical feature completing a spinal fusion surgery procedure in a timely manner.

U.S. Pat. No. 9,737,411B2 is to Loebl is different to the other implants mentioned in that it uses a worm drive mechanism to open link arms hinged from the ends of the base to create expansion. However, this design has similar disadvantages to Sharabani in that the large amount of internal space taken by the worm drive gear mechanism limits the range of implant heights that could treat a full range of clinically relevant disc sizes, while also limiting the size of the biological filler window since the material has to pass coaxially through the worm gear. In addition, a worm drive mechanism necessarily places significant stress on the small link arm gear teeth, limiting material choices only to very strong and stiff options, which is clinically less desirable than materials that better match the stiffness of the natural bone. The materials needed for the gear teeth are also less likely to provide radiolucency which is also another desired feature in interbody implants.

U.S. Patent Application 20170202679A1 to Butler also uses a worm drive as the driver for an expansion mechanism. While having the disadvantages noted for Loeble, the expansion ratio of Butler is more limited, thus providing a relatively small final footprint and a small biological filler enclosure. This design is also necessarily mechanically asymmetric about the body centerline which is not desirable since it creates uneven support for vertebral endplates, is more likely to dislodge during expansion, is more likely to subside into the endplates where it presents uneven surface contact, and finally creates an asymmetric radiological signature which may create difficulties in assessing fusion progress over time.

While many other expandable spinal implants of different designs exist in prior art, none have been found that meet the ideal combination of capabilities of the Application as presented in this disclosure. Accordingly, there is a need for an interbody spinal implant which can more optimally address the combination of several shortcomings noted for prior art spinal implants in one design.

SUMMARY OF THE DISCLOSURE

This summary of the disclosure is provided as a convenience to the reader, and does not limit or restrict the scope of the disclosure or the invention. This summary is intended as an introduction to more detailed description found in this Application, and as an overview of techniques explained in this Application. The described techniques have applicability in other fields and beyond the embodiments specifically reviewed in detail.

This Application describes a spinal implant, and techniques for use thereof, that:
  A. Can be inserted into a prepared disc in a minimally invasive configuration and be expanded in a controlled and predictable fashion in situ to provide the intended intervertebral support and lordotic correction;
  B. Has a robust mechanical design with strength and leverage to expand into collapsed areas of the disc, allowing the use of materials for construction that provide radiolucency and a more comparable structural stiffness to natural bone;
  C. Has a large expansion ratio to create a wide final footprint, a sufficiently large aperture with a unimpeded pathway for ease of biological filler insertion, and a large unimpeded internal enclosure for containing biological filler material;
  D. Provides structural stability in its expanded state to encourage boney fusion; and
  E. Has a design that allows for a practical manufacture of a wide range of short to tall implant heights to treat the full range of clinically relevant disc heights.

In one embodiment, a spinal implant can include a substantially U-shaped base having a floor and two walls, a screw coupled to the base, and travelers coupled to the screw, whereby turning the screw can cause the travelers to translate along the screw. The travelers can each be coupled to a link arm, the link arms being coupled to a displaceable element, whereby translating the travelers along the screw can cause the link arms to turn, to displace the displaceable element away from the floor, while maintaining the displaceable element substantially parallel to the floor. The link arms can be shaped so that, when turned, they are supported against the walls. This can have the effect that the displaceable element is supported by the turning link arms and does not lose its substantially parallel orientation with respect to the floor. For example, the displaceable element can be extended from within the U-shaped base to outside the U-shaped base.

In one embodiment, the screw can include a thread size and spacing so as to frictionally lock the screw from turning when not being explicitly turned, such as by an actuator. Similarly, the screw can include a thread size and spacing so as to frictionally lock the travelers from turning or translating when the screw is not being explicitly turned, such as by an actuator.

In one embodiment, the displaceable element can be maintained substantially flat with respect to the floor of the base. This can have the effect that the base, the link arms, and the displaceable element can collectively form an enclosure into which material that promotes bony growth can be dispensed. For example, the material can be dispensed through one or more apertures in the base, the link arms, or the displaceable element, while maintaining the enclosure substantially surrounded. The base, the link arms, and the displaceable element can collectively form the enclosure while providing a substantially high ratio of area for bony growth material relative to the region occupied by the spinal body implant.

In an alternative embodiment, the displaceable element can include pivotable segments. This can have the effect that when displaced from the floor (of the base), the displaceable element can be expanded, with at least one segment displaced further away than substantially flat with respect to the floor, so as to form a relatively larger enclosure.

In one embodiment, at least one surface of the implant, or at least one structure of the implant, can be coupled to a disc selected to accept the implant and can include materials disposed to encourage bony growth. Moreover, the implant can include prongs that are driven into the tissue of, or tissue surrounding, the selected disc, such as in a direction orthogonal to expansion of the implant (thus, parallel to the orientation of the spine).

In one embodiment, the relative height of the base, the link arms, and the displaceable element can be selected so as to substantially match an anatomic size, lordotic angle, and contour of a disc selected to accept said implant. For example, the base, the link arms, and the displaceable element can have their vertical displacements collectively form a wedge substantially matching the lordotic angle of the selected disc. This can have the effect that the implant can be disposed in the location of the selected disc without distorting the shape of the spine.

BRIEF DESCRIPTION OF THE FIGURES

The invention is herein described, by way of example only, with reference to the accompanying drawings. In the figures, like references generally indicate similar elements, although this is not strictly required.

FIGS. 2A-2E are orthogonal views of the implant in the fully collapsed, minimally invasive state.

FIGS. 5A-5E are orthogonal views of the implant in a latter phase of expansion while the displaceable element is further away from the U shaped nest of the base and the geometric features on the outside of the link arms are continuing to interact with the base to constrain its path of expansion.

FIGS. 6A-6E are orthogonal views of the implant in the fully expanded, maximum footprint state.

FIGS. 7A-7B are isometric views of the same implant shown in FIGS. 2A-2D.

FIGS. 8A-8B are isometric views of the same implant shown in FIGS. 4A-4D.

FIGS. 9A-9B are isometric views of the same implant shown in FIGS. 6A-6D.

FIGS. 12A and 13A illustrate the difference in the fully expanded footprint between the one embodiment of the implant and a variant of the implant with a displaceable element that is segmented with connecting hinges.

After reading this Application, those skilled in the art would recognize that the figures are not necessarily drawn to scale for construction, nor do they necessarily specify any particular location or order of construction.

DETAILED DESCRIPTION

By way of introduction, the present invention relates to a group of adjustable orthopedic implants applicable to a wide range of applications in which an expanding implant is required, and are particularly suitable for various minimally invasive spinal surgery (MISS) techniques, for inter-body or intra-body placement, and in various placement orientations and approach directions. The implants may be used to advantage, with minor adaptations that will be clear to a person having ordinary skill in the art, for a range of applications including, but not limited to: intervertebral fusion with intervertebral height restoration, lordotic correction and/or scoliosis correction, and other spinal and non-spinal orthopedic applications. The implants may be adapted to a variety of surgical approaches, including but not limited to: lateral lumbar interbody fusion (LLIF), transforaminal interbody fusion (TLIF), and posterior lumbar interbody fusion (PLIF). In each case, appropriate modifications are made to implant proportions, aspect ratios, and component shapes, as well as to specific features such as bone-purchase features, surface treatments, location of apertures for filling with biocompatible filler and/or osseous integration, and holding tool attachment locations, all as will be clear to a person having ordinary skill in the art after review of this Application.

The principles and operation of implants according to the present invention may be better understood with reference to the drawings and the accompanying description.

Figure 10A:
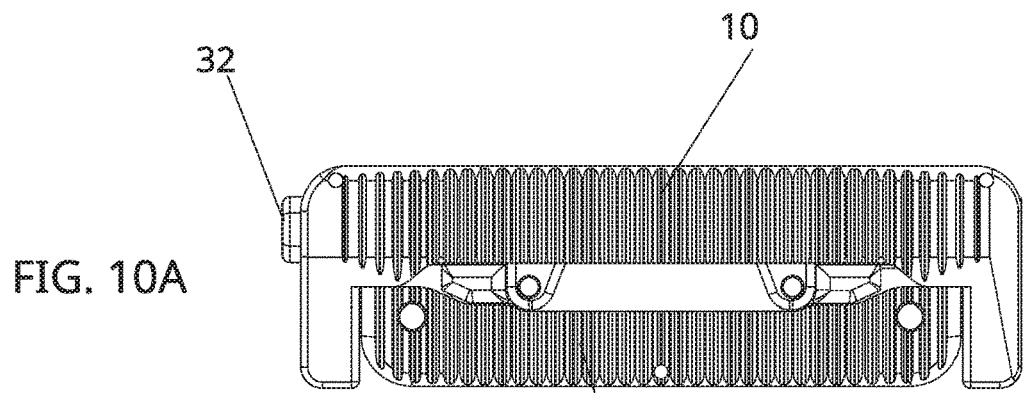
FIGS. 10A-10C are top views of a variant of the implant of FIGS. 1A-9B with shorter link arms, showing the progression of states between fully collapsed and fully expanded, whereby the displaceable element is still partially nested within the U shape of the base.
Figure 10B:
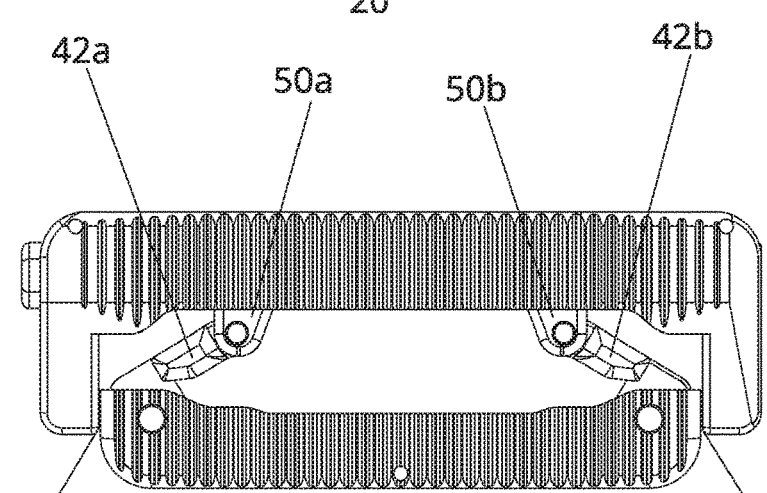
Figure 10C:
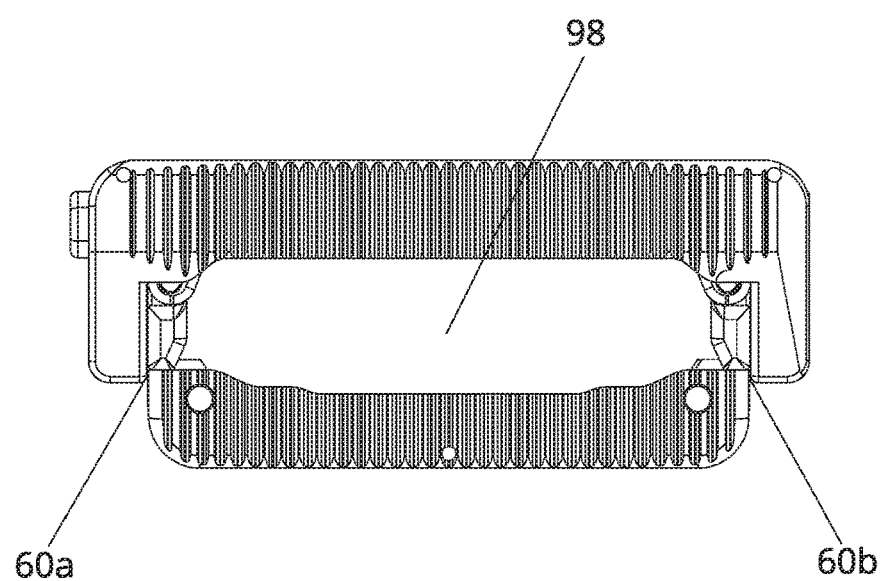

The present Application describes a number of possible embodiments, which are each of utility when used alone, but which may also be used to advantage in certain combinations. The first major embodiment, exemplified herein with reference to FIGS. 1A-9B, relates to an implant with deployment mechanism based on link arms 40a and 40b which are long enough to provide a final expanded configuration where the rigid displaceable element 20 lies entirely outside of the base 10. A second major embodiment of the invention exemplified herein with reference to FIGS. 10A-10C is a variant of the first embodiment implant having shorter link arms 42a and 42b which limit the expansion travel of the displaceable element 20 such that the displaceable element always remains at least partially nested within the base 10. A third major embodiment of the invention is exemplified herein with reference to FIGS. 11A-11C and 13A and relates to another variant of the first embodiment implant having a displaceable element that is segmented into segments 24a, 24b, and 24c with connecting hinge points 26a and 26b, allowing the displaceable element to bend in conjunction to the main linkage actuated expansion to create a larger overall implant profile in the final expanded state. This aspect with segmented displaceable element can be incorporated to both the first and second embodiments illustrated herein. All three major embodiments are illustrated herein as being optimized for deployment between a first and a second vertebral body using an LLIF approach, whereby the implant in its collapsed state is initially driven into the anterior aspect of a prepared disc and then expanded in-situ to provide support for the majority of the disc footprint while creating a central enclosure suitable for containing biological filler material.

According to the first major embodiment of the present invention as shown in FIGS. 1A-9B, the implant base 10 provides leading chamfers 11a and 11b on at least one end to facilitate in driving the collapsed form of the implant into a prepared disc. The base also includes biological filler apertures 12a and 12b for use when the implant has been expanded to insert of biological filler materials in-situ. Typically, only one of the filler apertures would be used through the primary surgical access path, but the mirrored aperture is provided to enable the implant to function similarly in a flipped orientation or to provide an alternate aperture if the surgical access is from both sides of the patient. The same biological filler apertures in the base may also serve dual function as engagement points for a separate elongated implant holding tool (not shown) to be used during the initial insertion of the collapsed implant into the disc. To further facilitate this engagement function, the filler apertures may incorporate minor modifications such as the addition of an internal thread profile. Alternatively, separate features other than the biological filler apertures may be added to the body of base 10 suitable for engagement with a separate implant holding tool.

Base 10 further includes barbed vertebral endplate contact surfaces 81, 82 on both sides to resist movement or expulsion post-implantation, and may be implemented as rows of barbs as illustrated, or as individual barb points. Similarly, the displaceable element 20 also provides barbed vertebral endplate contact surfaces 83, 84 on both sides. The barbed rows on the displaceable element surfaces are preferably oriented parallel to the direction of expansion to facilitate expansion of the displaceable element away from the base while resisting movement in directions generally orthogonal to expansion. In contrast to the base and displaceable element, the endplate contacting faces of the link arms 85 and 86 are preferably barbless because the movement of the link arms during expansion is multi-directional and the added mechanical friction between barbed surfaces of the link arms against the disc endplates may cause the implant to dislodge from its intended position within the disc during expansion.

Also according to the first embodiment of the present invention, the displaceable element 20 is supported and moved, relative to base 10 by a pair of link arms 40a and 40b. A first link arm 40a is pivotally connected to displaceable element 20 at pivot point 21a on one end and pivotally connected to first traveler 50a at pivot point 51a on the other end. A second link arm 40b is pivotally connected to displaceable element 20 at pivot point 21b on one end and pivotally connected to a second traveler 50b at pivot point 51b on the other end.

The actuation of motion of the two link arms is achieved by an actuator implemented as a threaded screw 30 extending within base 10 and mounted within base screw mounting holes 16a and 16b so as to be rotatable about the central axis of the threaded screw without translating relative to the base 10. In one method illustrated here, each traveler 50a and 50b is implemented as an internally threaded element which engages a corresponding externally threaded portion of the screw 30 which extends along a part of the length of base 10. In the configuration shown here, threaded screw 30 includes a first portion 31a with a thread and a second portion 31b with an opposite-handed thread. With the first and second travelers each engaged to the opposite handed threads as mirror opposites, rotation of threaded screw 30 thus causes displacement of the first and second travelers 50a and 50b in opposite directions. This displacement hence generates motion of the first and second link arms 40a and 40b, reversibly, through the range of positions illustrated in FIGS. 2A-9B.

It should be noted that the use of a threaded screw actuator in this context may offer the advantages of simplicity, intuitiveness, reliability, reversibility, and/or capacity to bear loads. When using a pair of link arms, the range of motion for each traveler 50a and 50b is limited to be within the length of base 10. Therefore, in order to maximize the potential length of displacement and hence the expansion ratio provided by the link arms 40a and 40b, it is beneficial to limit the threaded length of the travelers 50a and 50b as much as practically feasible, maximize the length of the screw thread segments 31a and 31b exposed for the travelers in base 10, and implement necessary screw constraints like screw flanges 34 and 35 at the ends of the screw rather than the middle to provide more length for traveler displacement.

In the implant as illustrated here, both link arms 40a and 40b are the same length and the thread pitch of the two oppositely threaded portions 31a and 31b of screw 30 are the same, resulting in symmetrical opening of the two arms. It should be noted that references herein to link arms refer to functional elements which may, for design purposes, each be implemented as either single or double structures. For example, as shown in exploded views of FIG. 1A-1B, it will be noted that link arms 40a and 40b are shown as single elements. However, the link arms may alternatively be bilaterally attached pairs of linkages on either side of the travelers 50a and 50b and displaceable element 20. As shown in FIGS. 9A-9B, the single structure link arms incorporate respective biological filler through-apertures 46a and 46b that coaxially align with the base bone filler apertures 12a and 12b when the implant is in its expanded state. The single structure link arms also incorporate scallop cuts 43a and 43b to facilitate packaging of the link arms closer to screw 30 when the implant is in its collapsed state.

If the link arms are implemented as bilaterally attached double pair structures instead, the need for discrete biological filler apertures 46a and 46b and scallop cuts 43a and 43b may be obviated. However, such link arms may present tradeoffs of being more difficult to assemble and less robust when compared to the preferred single structure link arms.

Figure 1A:
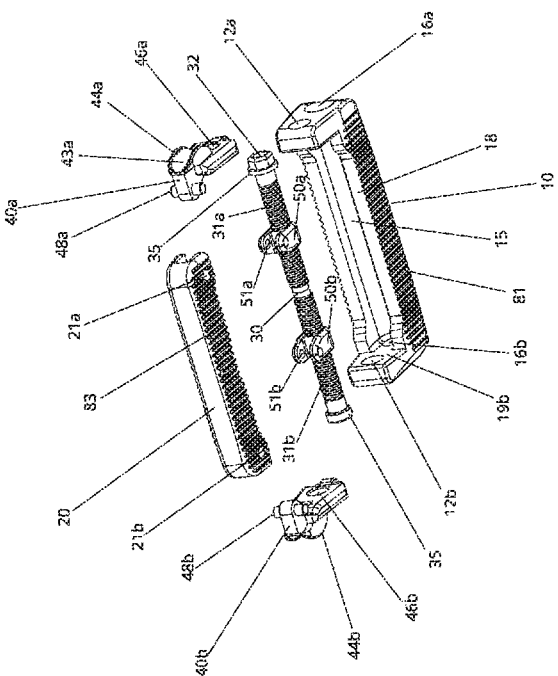
FIGS. 1A-1B are exploded isometric views of an implant illustrating the components according to an exemplary embodiment.
Figure 1B:
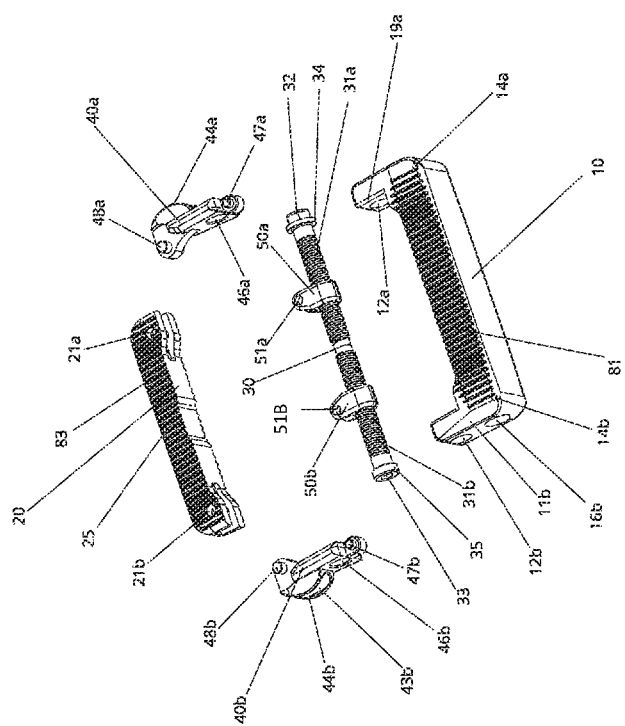

To constrain the travelers 50a and 50b from rotating about the central axis of screw 30, the travelers are mounted partially within the lengthwise cavity 15 in the base such that the non-round outer profile of the travelers on at least one side closely matches the sectional shape of the cavity. It should be noted here that in certain cases, it may be beneficial to have a looser fit between the travelers and base cavity to allow a limited amount of free rotation of travelers 50a and 50b about the central axis of screw 30—for example to accommodate a disc shape with non-planar surfaces when the implant is expanded. In order to maintain reliable engagement with screw 30, the bodies of travelers 50a and 50b as shown in FIGS. 1A-1B fully circumscribe the screw, but it may also be preferable to only partially circumscribe the screw, but leave a gap of less than 180 degrees around the screw to reduce the profile of the traveler and consequently allow for a smaller sectional profile of base 10. Another alternative means to maintain engaged spacing between the traveler and the screw in cases when a low profile traveler is desired is to trap the traveler against the screw inside an enclosed lengthwise cavity in the base while only leaving a narrow lengthwise slot to expose traveler pivot points 51a and 51b. In similar fashion, slots parallel to screw 30 could be cut into the base to slidably engage with a low profile traveler and maintain its engaged spacing to the screw.

As illustrated in FIGS. 1A-9B, the preferred geometry of this implant is a quadrilateral defined by the pivot axes of connections 21a, 21b, 51a, and 51b, and where increasing a spacing between the first and second traveler pivot locations 51a and 51b is effective to increase a spacing between the base 10 and the displaceable element 20. In order to implement this geometry, the locations of pivotal connections 21a and 21b are preferably near the ends of displaceable element 20, for example, with the axis of pivotal connection 21b within the distal-most 25% of the length of the displaceable element and with the axis of pivotal connection 21a within the proximal-most 25% of the length of the displaceable element. Link arms 40a and 40b are not mechanically interconnected to any other element than the travelers 50a and 50b mounted on screw 30 and displaceable element 20. A quadrilateral geometry with four pivot axes is not inherently a stable structure and could potentially allow displaceable element 20 to move in a rocking or folding motion in a direction parallel to the length of base 10. In surgical use, this could be a disadvantage because an implant that expands unpredictably within a collapsed disc could become dislodged from its intended position, negating its intended clinical benefit.

To prevent or limit any such rocking motion, the major embodiments described herein preferably have features deployed to limit rocking motion of displaceable element 20 relative to base 10 in a direction parallel to the length of the base while allowing a range of spacing between the base and displaceable element. In the first embodiment illustrated here, base 10 is shaped like an elongated letter U with the base U shape bottom aspect 18 longer than the base U shape side aspects 19a and 19b. In the early stage of expansion, displaceable element 20 is nested within the U shape of the base and the displaceable element to base sliding interaction 60a and 60b on both sides constrains the displaceable element from the aforementioned rocking motion relative to the base. This can be seen in FIGS. 2C and 3C. It will be noted that the relative motion of link arms 40a and 40b and the base as the implant expands is a compound motion made up of displacement plus rotation. In the latter stages of expansion, displaceable element 20 is entirely outside of the U shape nest of base 10 and is no longer directly constrained by sliding interaction 60a and 60b. However, by forming cam-shaped geometric contact profiles 44a and 44b on the outer faces of link arms 40a and 40b that fill the empty space between the link arms and side aspects 19a and 19b of the base during this phase of expansion, it is possible to use the link arms to base geometric interaction 70a and 70b as illustrated in FIGS. 4C, 5C, 8A and 8B to substantially eliminate unwanted rocking motion of displaceable element 20 relative to base 10. Geometric interactions 70a and 70b are also clinically useful to allow displaceable element 20 to reliably retract back into U shaped nest of base 10, as it may be desired in certain cases to revert the implant to a collapsed state and reposition the implant before re-expanding it, or to remove the implant from the disc entirely—for example, to further clear the disc space or to switch to a different size implant. Thus, by implementing sliding interaction 60a and 60b in combination with geometric interaction 70a and 70b, the implant is able to substantially eliminate unwanted rocking motion of the displaceable element 20 throughout its entire range of expansion and retraction. These solutions in whole or part may be used to eliminate rocking of the displaceable element in the all major embodiments described herein. It should be emphasized that this characteristic provides another significant clinical benefit to these implants—in certain surgical cases, ossification and partial fusion across a diseased disc prevents any disc height restoration near the ossification site, meaning the implant can only be expanded up to the point the disc's anatomical geometry will allow. In such cases, it is highly beneficial to be able to leave the implant in only a partially expanded state if it can still provide excellent structural stability.

Figure 3D:
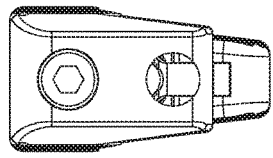
FIGS. 3A-3E are orthogonal views of the implant in an early phase of expansion while the displaceable element is partially nested within the U shape of the base.
Figure 3A:
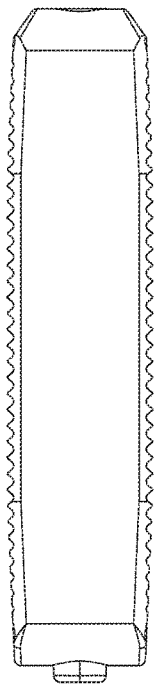
Figure 3C:
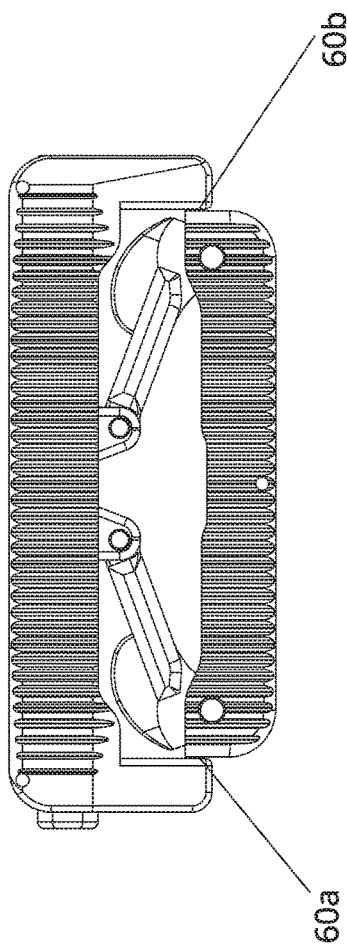
Figure 3E:
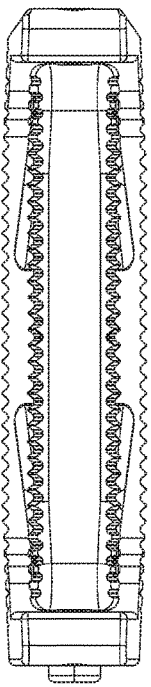
Figure 3B:
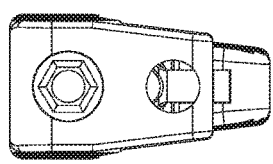
Figure 4D:
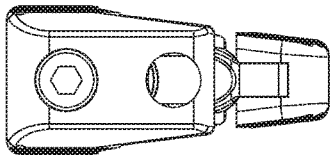
FIGS. 4A-4E are orthogonal views of the implant in a middle phase of expansion while the displaceable element has just exited the U shaped nest of the base and the geometric features on the outside of the link arms are interacting with the base to constrain its path of expansion.
Figure 4A:
Figure 4C:
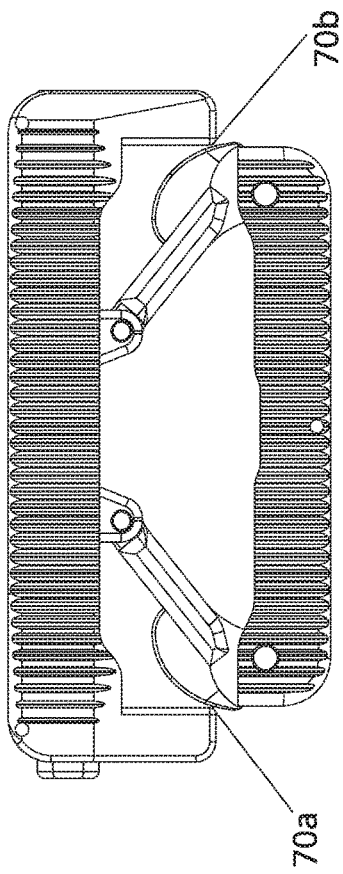
Figure 4E:
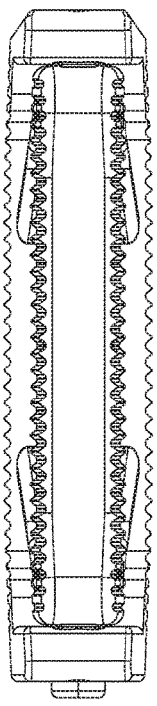
Figure 4B:
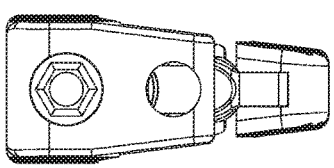

It should be noted here that the U shaped base 10 can also serve another useful function in the context of this Application, when the implant is used as an expandable spacer to treat a lordotic disc application. As illustrated in FIGS. 2A-6E, the height of the side aspects 19a and 19b of the base in a lordotic version of the implant are taller than the height of the displaceable element 20. Between the fully collapsed state and approximately halfway into the expansion phase when the mechanical leverage imparted by screw 30 through the link arm mechanism is relatively low due to the shallow angulation of the link arms 40a and 40b relative to the screw, the side aspects of the base effectively shield the displaceable element from significant compressive contact against the disc endplates. This is illustrated in FIG. 3D. Beyond the approximate halfway point in the expansion phase, the displaceable element's exposure to compressive contact against the disc necessarily increases, but this is matched by correspondingly increasing mechanical leverage imparted by screw 30 through the link arm mechanism as the angulation of link arms 40a and 40b become more orthogonal to the screw. Additionally, the orthogonal reactive force imparted by the disc endplates on the screw 30 through the connected chain of displaceable element 20, link arms 40a and 40b, and travelers 50a and 50b during implant expansion increases throughout the expansion, but this is also matched by the correspondingly improving mechanical support of the screw as the travelers move closer to the base screw mounting holes 16a and 16b. In sum, the mechanical design of this implant is optimized to apply the highest amount of mechanical leverage to expand the displaceable element where it is needed most, and also provide support for the screw against highest endplate reactive forces where it is needed most. This mechanical optimization provides secondary benefits to the overall implant design by allowing the use of a wider range of materials for construction that are better matched in characteristics to natural bone and provide optimized radiolucency, instead of forcing the use of specific materials that may be overly stiff and provide poor radiolucency.

To facilitate adjustment of the implant expansion inside the disc, screw heads 32 and 33 on each end of the screw 30 incorporate non-circular geometric features such as, but not limited to, a hex or Torx shaped female depression for engagement of an separate elongated actuator tool (not shown) with a matching male geometry suitable for turning the screw. The elongated actuator tool would optionally have a torque limiting clutch feature for each rotational direction to prevent accidental overtorque of the screw 30 at the limits of allowable displacement for travelers 50a and 50b, or if the disc presents with ossified and fused areas that prevent full expansion of the implant. Without disrupting the non-circular geometric features, the screw heads may additionally provide another potential point of engagement to a separate implant holding tool (not shown), taking the form of a coaxial hole or threaded hole in the center of the screw heads. The implant holding tool may be separate to the actuator tool or both tools may be coaxially combined for simplicity of use. Either of the separate tools or the combined tool may be further combined with the prior mentioned holding tool that engages with the base biological filler aperture 12a or 12b or alternate holding tool engagement features built into base 10. As a further consolidation of tools, the portion of the holding tool that engages biological filler apertures 12a and 12b can integrate a cannula that also serves as a conduit for delivery of biological filler material through the surgical access while the holding tool is still engaged to the implant.

After the desired insertion and expansion adjustment of the implant, the holding and actuator tool(s) are withdrawn leaving the adjusted implant in place within the body. The pitch of the threaded engagement between the screw threaded segments 31a and 31b with the travelers 50a and 50b is such that the state of the implant remains frictionally locked and can function as a load bearing structure. If repositioning or removal is required, the actuator tool and/or holding tool may be reinserted to allow retraction of the displaceable element 20 for removal or repositioning of the implant. Depending on the intended application, the implant can be filled with biological filler material suited to the particular application, such as morselized bone or other bone-growth enhancing material, through coaxially aligned biological filler apertures 12a and 46a or 12b and 46b which provide direct and unimpeded access to the enclosure 90 inside the expanded implant. These features are illustrated in FIGS. 9B and 12A. It should be emphasized here that the in-situ filling procedure for any interbody implant through a minimally invasive access is often a slow and tedious process in surgery, and direct access into the enclosure area through a sufficiently large aperture is a rare and valuable feature in an expandable implant for saving time and effort. In addition, it is also rare for an expandable implant to provide an uninterrupted internal enclosure like enclosure 90 for biological filler material to facilitate rapid formation of a bone bridge through the implant.

Finally, so long as major mechanisms are not negatively impacted, the rigid solid elements that comprise the implant may be strategically perforated with a plurality and variety of apertures or cavities to tune the implant for optimal structural compliance. The apertures or cavities would be sized so as not to detract from the ability of the implant to contain biological filler material, but may still allow interdigitation of boney fusion between the inside and outside of the enclosure within the disc In clinical practice, it is thought that an implant that can closely match the stiffness of natural bone is able to provide support for the disc while preventing excessive interface stresses from forming where the implant makes contact with the endplate.

Turning now to FIGS. 10A-10C, there is shown a variant second major embodiment of an adjustable implant, according to an aspect of the present invention. This implant is generally similar to the implant described as the first major embodiment above, and unchanged elements are either not labeled or labeled with the same numbers. This second embodiment of the implant simply has shorter link arms 42a and 42b than the longer arms 40a and 40b of the first embodiment implant, which keeps the displaceable element 20 in this case at least partially overlapped within the U-shaped base 10 during the full range of implant expansion. With this implant, the displaceable element is in constant sliding contact 60a and 60b with the base side aspects 19a and 19b to prevent rocking motion of the displaceable element during expansion. Therefore, the shorter link arms 42a and 42b of this implant have no need for link arm geometric contact profiles 44a and 44b similar to those present on the longer arms 40a and 40b to prevent rocking motion of the displaceable element 20 outside of the U shape of base 10. Because the displaceable element never loses contact with the base, it may be advantageous to implement sliding tracks between displaceable element 20 and base side aspects 19a and 19b where they have sliding interaction 60a and 60b. The tracks may take the form of a tongue and groove, dovetail, or any similar sliding joint familiar to a person having skill in the art.

This second embodiment of the implant with shorter link arms may allow more freedom to employ alternate types of link arm actuation configurations to expand the implant. For example, two similar link arms may be arranged such that decreasing the spacing between the travelers 50a and 50b rather than increasing the spacing is effective to expand the implant. Alternatively, one or more link arms on one or more travelers may be employed in a parallel arrangement on a screw with only a single thread rather than opposite handed thread segments to push the displaceable element asymmetrically while relying on the aforementioned sliding tracks between the base side aspect 19a and 19b and displaceable element 20 to provide stability for the displaceable element during expansion.

While this second embodiment of the implant may have a smaller expansion ratio and thus a smaller biological filler enclosure 98 than the implant of the first embodiment, this variant of the implant may have advantages in the ease of manufacture due to using components having fewer and simpler features.

Figure 11A:
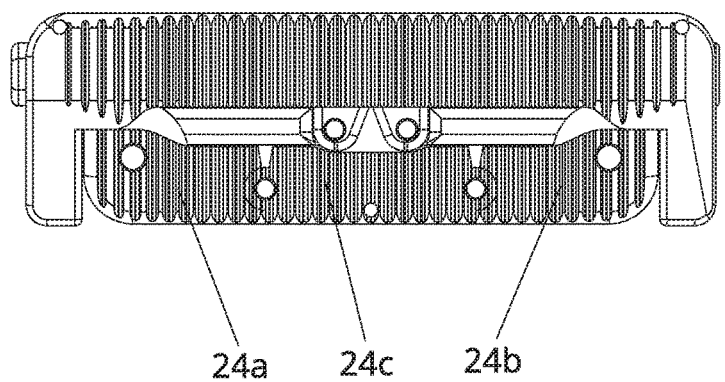
FIGS. 11A-11C are top views of a variant of the implant of FIGS. 1A-9B with a displaceable element that is segmented with connecting hinges, showing the progression of states between fully collapsed and fully expanded, whereby the displaceable element at the fully expanded state is caused to bend outward at its hinges to create a larger implant footprint and internal enclosure.
Figure 11B:
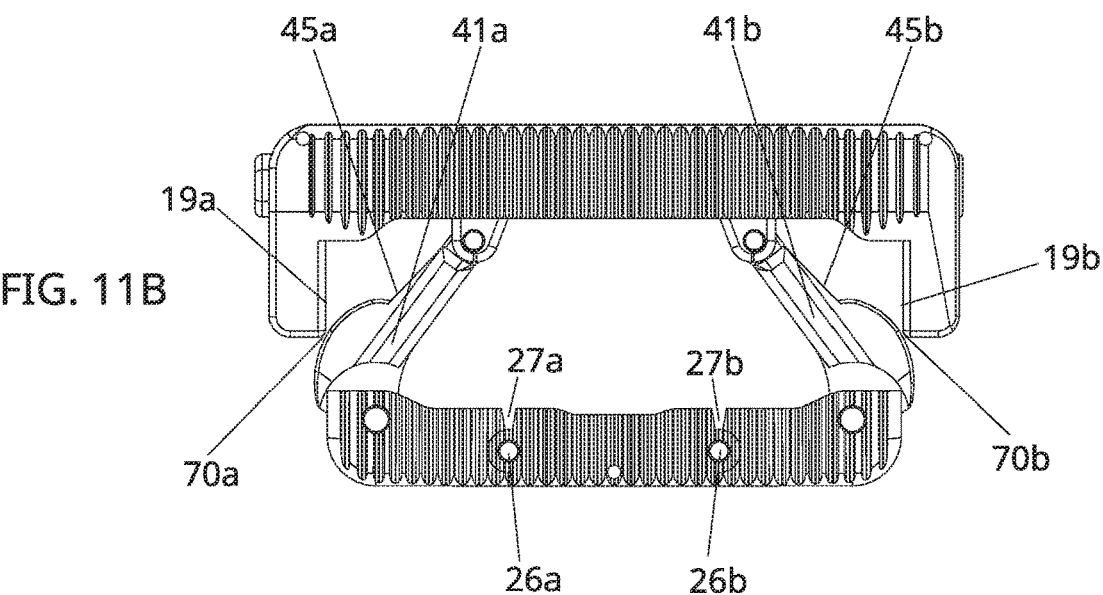
Figure 11C:
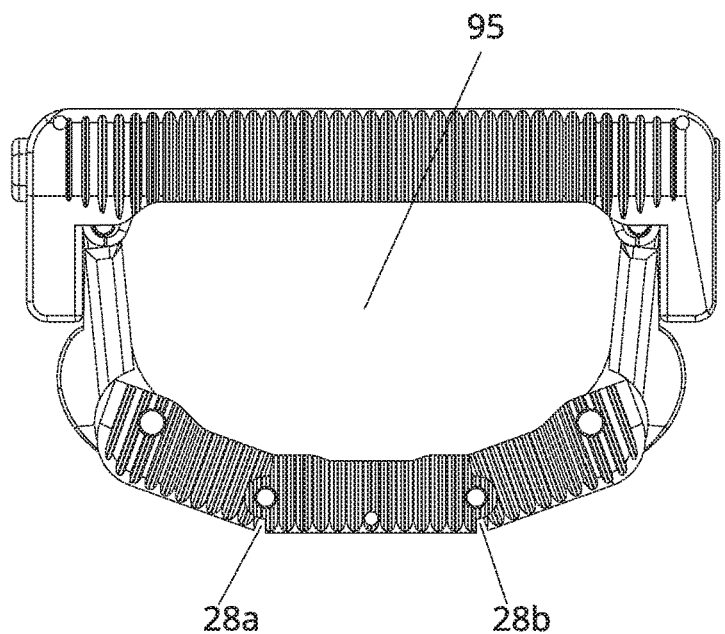

Turning now to FIGS. 11A-11C, there is shown a variant third major embodiment of an adjustable implant, according to an aspect of the present invention. This implant is also generally similar to the implant described as the first major embodiment in FIGS. 1A-9B above, and unchanged elements are labeled with the same numbers. The main difference between this third embodiment of the implant and the first embodiment is that the third embodiment implant employs a segmented displaceable element comprised of segments 24a, 24b, and 24c with hinge points 26a and 26b between the segments. Each hinge point includes inner hard stops 27a and 27b and outer hard stops 28a and 28b to control the angulation of each hinge in each direction. It should be noted that while three segments and two hinge points between them are illustrated here, the number of segments can be any number greater than one with hinge points placed between segments. The segments may also vary in length or profile to achieve a desired bent profile of the segmented displaceable element.

According to a further aspect of the third embodiment implant, special link arms 41a and 41b are included to act on the segmented displaceable element, as shown in FIGS. 11B and 11C. While similar to link arms 40a and 40b of the implant in the first embodiment, link arms 41a and 41b further incorporate angled spacers 45a and 45b on their outer faces that are designed to provide a convergent angulation of the link arms when they come into contact with the side aspects 19a and 19b of U shaped base 10. The angled spacers 45a and 45b on link arms 41a and 41b thus act to reduce the spacing between the link arm pivot points connected to the far ends of the segmented displaceable element, causing the segmented displaceable element to bend outward, resulting in a larger implant footprint and biological filler enclosure area 95 for this third implant embodiment than the enclosure area 90 of the implant in the first embodiment. The implant of the third embodiment is illustrated herein in the context of the first embodiment in FIGS. 12A and 13B. It should be noted that the preferential bending direction for the segmented displaceable element is dependent on whether the segment hinge points are located more inboard or outboard than the line defined by the two outer link arm pivot points, as would be familiar to a person having skill in the art after reading this Application.

While explicit illustrations are not provided, further alternative minor implementations of an implant which is generally structurally and functionally similar to implants of the first, second, and third embodiments described above can be constructed. In one such a case, the two link arms are of different lengths, resulting in lesser mechanical amplification on one side of the displaceable element and a corresponding asymmetric opening of the implant. It should be noted that the degree of mechanical amplification for each side can additionally, or alternatively, be varied by using different thread pitches for each traveler.

In another alternative implant, one end of the displaceable element is directly connected by hinge to the corresponding side aspect of the base, while a single link arm provides mechanical amplification of the second end of the displaceable element, thereby allowing control of both the spacing and the angular relationship between the base and the displaceable element.

In yet another alternative implant, the displaceable element may be connected by hinges to the base on both ends and split into two segments such that the action of associated link arms on the opposite ends of each segment results in a change of angle of the displaceable element segments relative to said base and the formation of two enclosed pockets within the expanded implant.

To the extent that the appended claims have been drafted without multiple dependencies, this has been done only to accommodate formal requirements in jurisdictions which do not allow such multiple dependencies. It will be appreciated that the above descriptions are intended only to serve as examples, and that many other embodiments are possible within the scope of the present invention as defined in the appended claims.

After reading this Application, those skilled in the art will recognize that the techniques described herein are applicable to a wide variety of different types of spinal structures and spinal surgeries, and substitutes therefor; to a wide variety of different ways in which the spinal structures could be operated upon; to a wide variety of related devices that could be used with the spinal structures and spinal surgeries; or otherwise.

This Application describes a preferred embodiment with preferred structures, and, where applicable, preferred process steps, and that implementation of alternative structures or process steps would not require undue experimentation or further invention. The claims are incorporated into the specification as if fully set forth herein.

REFERENCE NUMERALS

10 Base
11a/b Base Leading Chamfers
12a/b Base Biological Filler Apertures
14a/b Base Radiolucent Markers
15 Base Cavity
16a/b Base Screw Mounting Holes
18 Base U Shape Bottom Aspect
19a/b Base U Shape Sides Aspect
20 Displaceable Element
21a/b Displaceable Element Pivot Points
24a/b/c Displaceable Element Segments
25 Displaceable Element Radiolucent Marker
26a/b Displaceable Element Segment Hinge Points
27a/b Displaceable Element Segment Hinge Inner Hard Stops
28a/b Displaceable Element Segment Hinge Outer Hard Stops
30 Screw
31a/b Screw Opposite Threads
32 Screw Head with Interface Near Side
33 Screw Head with Interface Far Side
34 Screw Flange Near Side
35 Screw Flange Far Side
40a/b Link Arms
41a/b Link Arms for Segmented Displaceable Element
42a/b Short Link Arms for Nested Displaceable Element
43a/b Link Arms Scallops for Screw Clearance
44a/b Link Arms Geometric Contact Profile
45a/b Link Arm Angled Spacers for Bending Segmented Displaceable Element
46a/b Link Arm Biological Filler Apertures
47a/b Link Arms to Travelers Pivot Pins
48a/b Link Arms to Displaceable Element Pivot Pins
50a/b Travelers
51a/b Traveler Pivot Points
60a/b Displaceable Element to Base Sliding Interaction
70a/b Link Arm to Base Geometric Interaction
81 Base Barbed Upper Tissue Contact Surface
82 Base Barbed Lower Tissue Contact Surface
83 Displaceable Element Barbed Upper Tissue Contact Surface
84 Displaceable Element Barbed Lower Tissue Contact Surface
85 Link Arm Upper Tissue Contact Surface
86 Link Arm Lower Tissue Contact Surface
90 Standard Bone Filler Enclosure 95 Segmented Displaceable Element Bone Filler Enclosure
98 Nested Implant Bone Filler Enclosure

The invention claimed is:

1. A spinal interbody implant, including
a base defining a floor and walls, the floor being disposed in a first direction and the walls being disposed in a second direction substantially perpendicular to the floor, the base defining a cavity extending in the first direction across at least a portion of the floor, the cavity defining an opening facing substantially in the second direction;
a threaded screw mounted at least partially within the cavity and substantially parallel to the first direction, the screw being disposed to turn in response to an actuator;
a first traveler coupled to the screw and disposed to translate along the screw when the screw turns;
a first link arm coupled to the first traveler and disposed to rotate, between a first position near the floor and a second position near a first wall, in response to when the first traveler translates along the screw;
a displaceable element disposed substantially parallel to the floor, coupled to the first link arm, and disposed to translate between a first position near the floor and a second position away from the floor, in response to when the link arm rotates;
the first link arm being coupled to the displaceable element using a pivotable element, the pivotable element being disposed to rotate when the displaceable element is displaced away from the base;
wherein the first link arm consists of a single piece directly coupled to the displaceable element and the first traveler.

2. The implant as in claim 1, wherein
the base is substantially U-shaped and has a length of the floor longer than at least one of the walls,
the displaceable element is at least partially nested within the U-shaped base when in the first position near the floor.

3. The implant as in claim 1, wherein
the base is substantially U-shaped;
at least a portion of the displaceable element is maintained substantially within the U-shaped base during at least a first portion of translation of the displaceable element;
at least a portion of the displaceable element is maintained substantially outside the U-shaped base during at least a second portion of translation of the displaceable element.

4. The implant as in claim 1, wherein
the screw includes a selected thread pitch and material disposed to frictionally lock the traveler from translating when the screw is not engaged to an actuator.

5. The implant as in claim 1, wherein
at least one surface or structure couplable to a disc selectable to accept the implant includes materials disposed to encourage bony growth.

6. The implant as in claim 1, wherein
translation of the first traveler changes an angle of the displaceable element relative to the base.

7. The implant as in claim 1, including
a second traveler coupled to the screw and disposed to translate along the screw when the screw turns, in an opposite direction from the first traveler;
a second link arm coupled to the second traveler and disposed to rotate, between a first position near the floor and a second position near a second wall, in response to when the second traveler translates along the screw, the second link arm being disposed to at least partially nest within the base during substantially all of its rotation;
wherein the displaceable element is coupled to the second link arm and disposed to be supported by both the first link arm and the second link arm when
translating between a first position of the displaceable element and a second position of the displaceable element, whereby the displaceable element is maintained substantially parallel to the floor while translating.

8. The implant as in claim 7, wherein
the screw includes a first segment and a second segment, the first and second segments being opposite-handed;
the first segment being coupled to the first traveler and the second segment being coupled to the second traveler;
whereby when the screw turns, the first traveler translates in an opposite direction from the second traveler.

9. The implant as in claim 7, wherein
the first and second link arms are coupled to the displaceable element and disposed to change a distance between the displaceable element and the floor when changing a distance between the first and second travelers.

10. The implant as in claim 7, including
at least one aperture disposed in one or more of: the base, or at least one of
the first and second link arms, or the displaceable element;
wherein the base, the first and second link arms;
collectively define an enclosure into which material can be dispensed through the at least one aperture;
whereby the material can be interdigitated into or through the implant.

11. The implant as in claim 10, including
a plurality of apertures or cavities disposed to tune structural compliance of said implant to match the stiffness of natural bone, and
disposed to allow interdigitation of bone graft material into and through said implant.

12. A spinal interbody implant, including
a base defining a floor and walls, the floor being disposed in a first direction and the walls being disposed in a second direction substantially perpendicular to the floor, the base defining a cavity extending in the first direction across at least a portion of the floor, the cavity defining an opening facing substantially in the second direction;
a threaded screw mounted at least partially within the cavity and substantially parallel to the first direction, the screw being disposed to turn in response to an actuator;
a first traveler coupled to the screw and disposed to translate along the screw when the screw turns;
a first link arm coupled to the first traveler and disposed to rotate, between a first position near the floor and a second position near a first wall in response to when the first traveler translates along the screw;
a displaceable element disposed substantially parallel to the floor, coupled to the first link arm, and disposed to translate between a first position near the floor and a second position away from the floor, in response to when the link arm rotates;
a second traveler coupled to the screw and disposed to translate along the screw when the screw turns, in an opposite direction from the first traveler;

a second link arm coupled to the second traveler and disposed to rotate, between a first position near the floor and a second position near a second wall, in response to when the second traveler translates along the screw;

wherein the displaceable element is coupled to the second link arm and disposed to be supported by both the first link arm and the second link arm when translating between the first position and the second position, whereby the displaceable element is maintained substantially parallel to the floor while translating;

at least one aperture disposed in one or more of: the base, or at least one of the first and second link arms;

where in the base, the first and second link arms, and the displaceable element collectively define an enclosure into which material can be dispensed through the at least one aperture, while maintaining that enclosure substantially surrounded in those directions within a plane including the base and the displaceable element;

whereby the material can be interdigitated into or through the implant; wherein a ratio of area of the enclosure to a collective area of the base, the first and second link arms, and the displaceable element, exceeds about 0.75:1.

13. The implant as in claim 12, wherein the displaceable element includes a plurality of sections, at least two of the sections being coupled by a hinge;

whereby the displaceable element bows outward when translated away from the floor, with at least a portion thereof displaced further away than if all the sections were substantially parallel with respect to the floor.

14. A spinal interbody implant, including a base defining a floor and walls, the floor being disposed in a first direction and the walls being disposed in a second direction substantially perpendicular to the floor, the base defining a cavity extending in the first direction across at least a portion of the floor, the cavity defining an opening facing substantially in the second direction;

a threaded screw mounted at least partially within the cavity and substantially parallel to the first direction, the screw being disposed to turn in response to an actuator;

a first traveler coupled to the screw and disposed to translate along the screw when the screw turns;

a first link arm coupled to the first traveler and disposed to rotate, between a first position near the floor and a second position near a first wall, in response to when the first traveler translates along the screw;

a displaceable element disposed substantially parallel to the floor, coupled to the first link arm, and disposed to translate between a first position near the floor and a second position away from the floor, in response to when the link arm rotates:

a second traveler coupled to the screw and disposed to translate along the screw when the screw turns, in an opposite direction from the first traveler;

a second link arm coupled to the second traveler and disposed to rotate, between a first position near the floor and a second position near a second wall, in response to when the second traveler translates along the screw;

wherein the displaceable element is coupled to the second link arm and disposed to be supported by both the first link arm and the second link arm when translating between the first position and the second position, whereby the displaceable element is maintained substantially parallel to the floor while translating;

the displaceable element includes a plurality of sections, at least two of the sections being coupled by a hinge;

whereby the displaceable element bows outward when translated away from the floor, with at least a portion thereof displaced further away than if all the sections were substantially parallel with respect to the floor;

wherein the base, the first and second link arms collectively define an enclosure into which material can be dispensed through the at least one aperture, wherein, a ratio of area of the enclosure to a collective area of the floor, the first and second link arms, and the displaceable element, exceeds about 0.75:1.

15. The implant as in claim 14, wherein the plurality of sections includes at least one section displaced substantially parallel to the floor and further away than if all the sections were substantially parallel with respect to the floor.

16. The implant as in claim 14, wherein the displaceable element is disposed to bend by an interaction of the first and second link arms, whereby spacing between locations where the first and second link arms couple to the displaceable element is reduced.

17. The implant as in claim 16, wherein the first and second link arms, and the displaceable element, are oriented substantially horizontally with respect to a disc selectable to accept the implant;

a height of one or more of the base, the first and second link arms, or the displaceable element substantially accommodates one or more of: an anatomic size, or contour, of an annulus of a disc selected to accept the implant, or a lordotic angle between a set of two adjacent disc endplates.

18. The implant as in claim 17, wherein the first and second link arms, and the displaceable element, are oriented substantially horizontally with respect to a disc selectable to accept the implant, the base, the first and second link arms, and the displaceable element, are disposed to have vertical displacements collectively form a wedge substantially matching the lordotic angle between a set of two adjacent disc endplates of the selected disc.

19. The implant as in claim 17, wherein whereby the displaceable element bows outward when translated away from the floor, with at least a portion thereof displaced further away than if all the sections were substantially parallel with respect to the floor.

\* \* \* \* \*